(12) United States Patent
Souers

(10) Patent No.: US 7,185,531 B2
(45) Date of Patent: Mar. 6, 2007

(54) MATERIAL LOSS MONITOR FOR CORROSIVE ENVIRONMENTS

(75) Inventor: Philip Forrest Souers, Chuluota, FL (US)

(73) Assignee: Siemens Power Generation, Inc., Orlando, FL (US)

(*) Notice: Subject to any disclaimer, the term of this patent is extended or adjusted under 35 U.S.C. 154(b) by 201 days.

(21) Appl. No.: 10/956,428

(22) Filed: Oct. 1, 2004

(65) Prior Publication Data
US 2005/0126269 A1 Jun. 16, 2005

Related U.S. Application Data

(60) Provisional application No. 60/528,875, filed on Dec. 11, 2003.

(51) Int. Cl.
*G01N 17/00* (2006.01)
(52) U.S. Cl. ........................................... 73/86
(58) Field of Classification Search ............... 73/86; 340/605; 116/208
See application file for complete search history.

(56) References Cited

U.S. PATENT DOCUMENTS

| | | | | |
|---|---|---|---|---|
| 2,991,439 A | * | 7/1961 | Marsh et al. ................. | 338/13 |
| 3,621,810 A | * | 11/1971 | Zuck ........................... | 116/283 |
| 3,639,876 A | * | 2/1972 | Wilson ......................... | 338/13 |
| 3,846,795 A | * | 11/1974 | Jones .......................... | 340/540 |
| 4,628,252 A | | 12/1986 | Terhune et al. | |
| 4,655,077 A | * | 4/1987 | Purvis et al. ................. | 73/86 |
| 5,297,940 A | | 3/1994 | Buse | |
| 5,446,369 A | | 8/1995 | Byrne | |
| 5,571,955 A | * | 11/1996 | Beavers et al. ............... | 73/86 |
| 5,728,943 A | | 3/1998 | Colter, Jr. et al. | |
| 5,740,861 A | * | 4/1998 | Williams ..................... | 166/66 |
| 6,131,659 A | | 10/2000 | Johnson | |
| 6,194,902 B1 | | 2/2001 | Kuo | |
| 6,366,201 B1 | * | 4/2002 | Hanisko ...................... | 340/454 |
| 6,487,895 B2 | * | 12/2002 | Brooker et al. .............. | 73/86 |
| 6,564,620 B1 | * | 5/2003 | Jaeger .......................... | 73/86 |
| 6,568,251 B1 | * | 5/2003 | Huijbregts et al. ........... | 73/86 |

* cited by examiner

*Primary Examiner*—Robert Raevis

(57) ABSTRACT

The present invention relates to monitoring the corrosive damage caused to items in a corrosive environment by using multiple monitored coupons 30 of varying thickness that, when corroded, transmit information to a monitor 40 allowing a user to estimate the corrosive damage valuable industrial components 20. The corrosion rate of the coupons 30 can be used to optimize the environmental conditions, so that items in the environment corrode at desired rates.

17 Claims, 3 Drawing Sheets

US 7,185,531 B2

MATERIAL LOSS MONITOR FOR CORROSIVE ENVIRONMENTS

CROSS-REFERENCE TO RELATED APPLICATIONS

This invention claims priority to U.S. Provisional application 60/528,875, filed on Dec. 11, 2003, entitled "Material Loss Monitor," which is incorporated herein by reference.

FIELD OF THE INVENTION

The field of the invention relates to monitoring the damage caused to items in a corrosive environment. More particularly, the present invention estimates damage to parts in a corrosive environment and aids in determining optimal environment conditions.

BACKGROUND

Many industries have machinery and parts that are intermittently or continuously exposed to corrosive environments. Due to the nature of these environments, direct observation of the corroding parts is usually impossible since they tend to be in inaccessible areas. In most cases, actual measurements of corrosion levels require that entire systems be brought off line and opened up.

Bringing systems off line, however, can be very expensive and time consuming, therefore corrosion rates tend to be estimated. Since failure of some parts can be catastrophic, the corrosive levels of the parts are overestimated which results in the operation of the processes in which they are used are kept on the conservative side. This reduces the risk of a failure due to excessive corrosion, however by overestimating the corrosion levels, process efficiency is typically lost. Therefore, without a more accurate estimation of corrosion levels, efficiency needs to be sacrificed to prevent part failure.

An example of a such system that has a corrosive environment is shown in FIG. 1. This figure illustrates a heat recovery steam generator (HRSG), which is used to turn otherwise wasted hot gasses into useful steam. Hot gasses enter 2 the HRSG from sources such as a gas turbine (not shown). Depending on the nature of the fuel used in the gas turbine, the hot gasses will contain varying levels of corrosive substances. In a HRSG, the hot gasses pass over heat transfer surfaces made up of tubes in which water, under pressure is converted to steam. The steam rises in the tubes and is collected in a series of three drums, a high pressure (HP) drum 6, an intermediate pressure (IP) drum 8, and a low pressure (LP) drum 10. Ultimately, the hot gasses are vented 4 after being depleted of most of their useful heat.

In the type of HRSG represented in FIG. 1, the heat from the hot gasses are transferred to either water, steam, or a combination of water and steam through use a boiler tube, which is a type of heat exchanger. An example of a typical boiler tube 20 at the rear of the HRSG is shown in FIG. 2. In this figure, the hot gasses 24 first pass over evaporation tubes 12 that heat water contained in the tubes to the point where the water is converted partially into steam. This water-steam mixture enters the LP drum 10, where the steam is separated 11. In this process, the LP drum requires make up water 22 to replace the volume lost by conversion to steam 11 and other causes. In order to capture the greatest amount of heat from the now cooled exhaust gas, the coldest water entering the system is first heated by passing it through a boiler tube. The boiler tube 20 runs water 22 through a center passage, while the hot gasses 24 pass over the outer surfaces, usually comprised of fins 26, to transfer the heat from the gas to the water. The hot gasses 24, however, contain corrosive elements, such as sulfur, that will erode the boiler tube 20. If the boiler tube corrodes to the point of breach, the entire HRSG system becomes subject to damage and will need to be taken offline.

The boiler tubes that carrying water to the LP drum 10 of the HRSG are particularly susceptible to corrosion, since at lower temperatures, generally between 110–250° F. (43–121° C.), corrosive elements condense out of the hot gas and form acids. In fact the section of the boiler tube that first receives the make up water 28 is the most susceptible to corrosion because it is the coldest part of the boiler exposed to the hot gasses 24. The HRSG system has a life expectancy of about 25 years, and if a boiler tube fails before this time, replacement costs an enormous amount of time and money. To prevent failure of the boiler tube 20, the temperatures of the tubes carrying water to the LP drum 10 are kept higher than they may other wise be, so that less corrosive elements condense out of the hot gas, causing a higher temperature gas to be vented to the environment, which is a waste of heat energy as well as a source of heat pollution. Over the course of 25 years this represents a substantial loss of revenue to the operator, and the waste of energy and excess heat pollution can have a large negative effect on the environment.

What is needed is a method and apparatus that can monitor the corrosion levels of component parts in corrosive environments.

SUMMARY OF THE INVENTION

With the foregoing in mind, methods and apparatuses consistent with the present invention, which inter alia facilitates the monitoring of the corrosion level of part in a corrosive environment. Machinery parts in a corrosive environment are notoriously difficult to observe, since the creation of the corrosive environment generally requires separation from the standard environment. The difficulty in observing corrosion can lead to whole systems failing due to corrosion of essential part. To overcome this, in the prior art corrosion level had been estimated. The estimates of the prior art, however, tend to be on the conservative side and result in inefficiencies either by running systems at sub-optimal levels, making more expensive parts or by replacing corroding parts too soon.

These and other objects, features, and advantages in accordance with the present invention are provided particular embodiments by a plurality of coupons of varying thickness that are exposed to the same corrosive environment as the part that is desired to be monitored. Often temperature is a factor in determining corrosion rate. The corrosive environment of the coupon is kept the same temperature of the part by the intimate contact of the coupon with the part so that their corrosion rates are the same. As the coupons are corroded through, they trip a monitoring device, which will notify a user of the coupon's failure. Since the coupons are of varying thickness, the user may chart the rate of corrosion and estimate when failure due to corrosion will occur. In systems such as a HRSG where corrosive conditions directly correlate with system efficiency, a maximum corrosive environment can be maintained without a premature failure of the monitored part.

In one embodiment the present invention provides for a method of monitoring corrosion of a part in a corrosive environment. The method comprises installing on the part multiple coupons of varying thickness, where the coupons are at least in part exposed to the corrosive environment. The coupons are linked to a monitoring device, which may be remote from the corrosive environment, where the monitoring device will register a failure in at least one of the multiple coupons. The failure is then interpreted as an approximate level of corrosion in the part.

In one embodiment the present invention provides an apparatus for monitoring corrosion of a part in a corrosive environment. The apparatus comprises one or more coupons that are exposed to the corrosive environment in a manner similar to the part. The apparatus further comprises a monitoring device that registers a failure in the one or more coupons. The coupons are either mounted to the part, the monitoring device, another feature in the environment or a combination thereof. The failure of a coupon correlates to an approximate level of corrosion in the part.

In a particular embodiment the present invention provides for a method and apparatus of monitoring corrosion of a boiler tube in a heat recovery steam generator. The method comprises installing on the boiler tube multiple coupons of varying thickness, where the coupons are at least in part wrapped around a surface of the boiler tube that is exposed to the corrosive environment. The coupons maintain substantial thermal contact with the boiler tube and are linked to a monitoring device. The monitoring device will register a failure in at least one of the coupons, where the failure in at least one of the coupons is a breaking of at least one of the coupons. The registering of the failure of at least one coupon comprises placing a coupon under tension that holds a spring under tension at a terminal end of the coupon, where the breaking of the coupon releases the spring, and the release of the spring closes a particular circuit, and where the closure of the particular circuit indicates a specific failure of a coupon of specific thickness. The specific failure in the coupon of specific thickness is then interpreted as an approximate level of corrosion in the boiler tube. In a more particular embodiment multiple interpretations are made on multiple failures of coupons of specific thickness to determine an approximate rate of corrosion in the boiler tube.

BRIEF DESCRIPTION OF THE FIGURES

The invention is explained in more detail by way of example with reference to the following drawings.

DETAILED DESCRIPTION OF THE INVENTION

The present invention provides for a corrosion rate monitoring method and apparatus. In one embodiment the invention provides multiple coupons of varying thickness that are exposed to the same corrosive environment as a part that is desired to be monitored. As the coupons are corroded through, they trip a monitoring device, which will notify a user of the coupon's failure. Since the coupons are of varying thickness, the user may chart the rate of corrosion and estimate when failure due to corrosion will occur. In systems such as a HRSG where corrosive conditions directly correlate with system efficiency, a maximum corrosive environment can be maintained without a premature failure of the monitored part.

Figure 3:
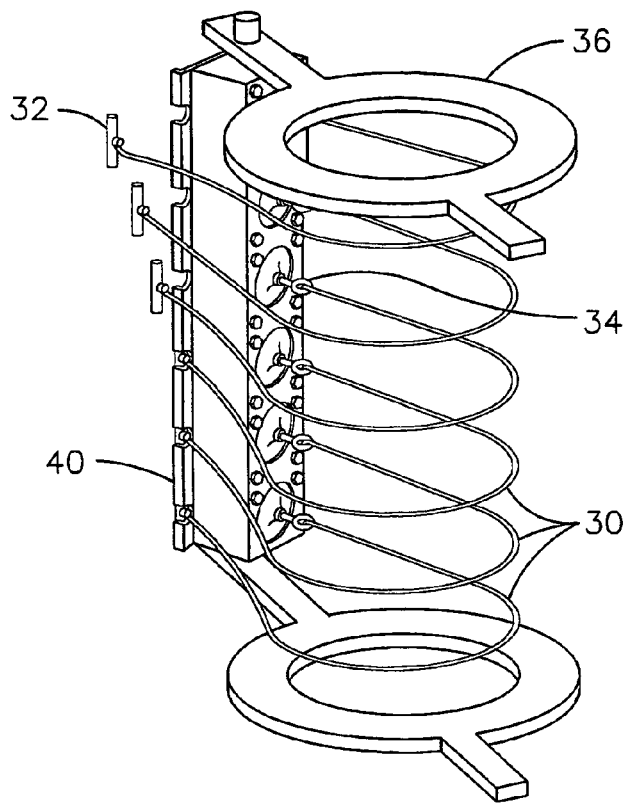
FIG. 3 illustrates a material loss monitor according to one embodiment of the present invention.

Referring to FIG. 3, one embodiment of the present invention is shown in which the material loss monitor comprises multiple coupons 30 that draw an elliptical path and connect to a monitoring device 40. In this embodiment, the entire material loss monitor can be placed into the corrosive environment. A second monitoring device (not shown) outside of the environment and connected to the first monitoring device 40 allows a user to check the status of the coupons 30.

In FIG. 3, the coupons 30 are arranged to wrap around a cylindrical part such as a pipe or boiler tube. In this embodiment, one end of the coupon 30 is attached to the monitoring device 40 via an eyebolt 34, while the other end is attached back to a fixed point on the monitoring device 40 using a dowel 32 which provides tension to the coupon 30. In this embodiment the eyebolt 34 may be part of the monitoring device 40 and in a in a particular embodiment is intricate to determining coupon failure (discussed below). In this manner, a plurality of coupons 30 are attached to an eyebolt 34 wrapped partially around a part to be monitored, and then pulled taut using the dowel 32 and attached back to the monitoring device 40. The free end of the coupon could also be attached to another anchor point, however other anchor points may not be readily available when the material loss monitor is being installed.

Figure 4:
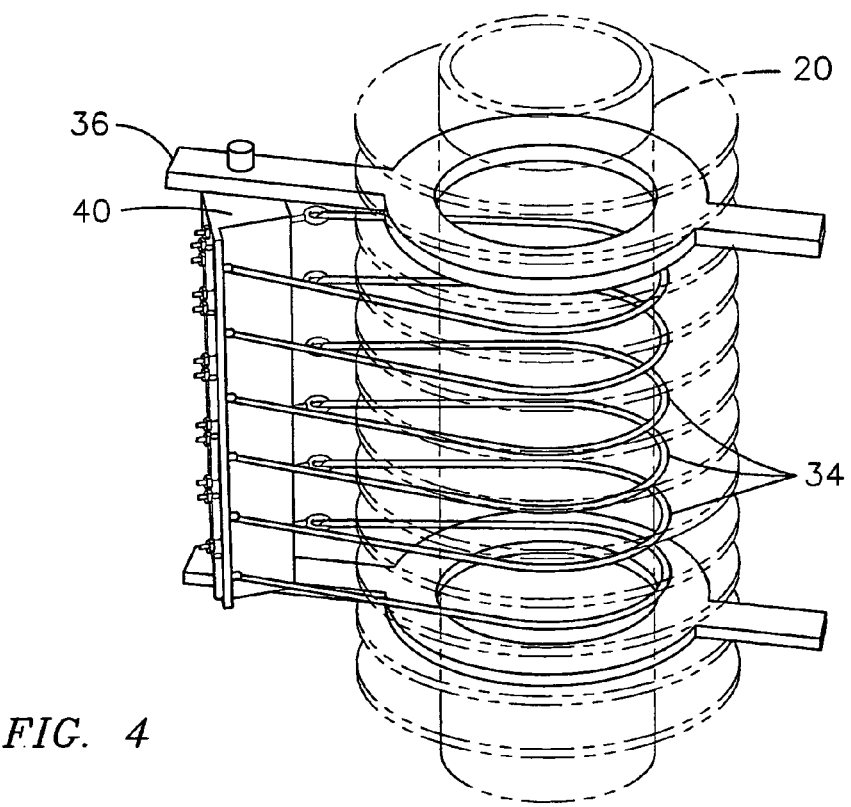
FIG. 4 illustrates one embodiment of a material loss monitor mounted to a boiler tube.

Also shown in FIG. 3 is a mounting device 36. In this embodiment the mounting device is installed on the part to be monitored. This embodiment of the device being mounted is also illustrated in FIG. 4, where the mounting device 36 is viced to a boiler tube 20. In other embodiments, the mounting device can be a variety of objects and designs, such as a clamp, vice, chain, stand or integrated with the unit to be monitored such as a tab In particular embodiments, the mounting device aids in keeping the coupons 34 taut as well as stabilizing the monitoring device 40.

In the FIGS. 3–4 the coupons 34 appear to be uniform wires, which is for illustration purposes only, and in many embodiment the coupons will be of varying thicknesses and a variety of shapes. In certain embodiment, when it is desired to monitor a particular corrosion point, it is preferable to have a single coupon of a certain thickness, or multiple coupons of a similar thickness. In alternate embodiments, however, it is desirable to use the present invention to monitor successive stages of corrosion, and multiple coupons of varying thickness are used. The initial coupon thickness is a known measurement, and is linked to a particular point on the monitoring device. In particular embodiment, the coupons are thicker in places along their length where failure is undesired. For example, in FIG. 4, it is desirable to measure the corrosion where the coupon 34 touches the boiler tube 20 where the corrosion rate is the greatest. However, in certain environs the portions of the coupons are entirely exposed to the open corrosive environment, they may fail faster than the part of the coupon that is in intimate contact with the monitored part. Therefore, in this embodiment the thickness of the coupons not in contact with the monitored part is increased to prevent premature failure at that point. Alternately, the coupons can be insulated along the length where premature failure is undesired.

Coupon shape is also varied depending on the embodiment. In many embodiments a wire coupon may be too fine and fail mechanically from vibration or other mechanical forces and may also corrode too quickly due to the large surface area per volume. Ribbon-shaped coupons are therefore preferred in some embodiments as they add to the cross-section area without adding thickness to the coupon. In addition the ribbon-shape coupon provides a more precise measurement of corrosion in relation to thickness since the corrosion at the sides of the ribbon-shaped coupon have little effect on the coupon's failure. Other shapes of coupons include, but are not limited to spiral, square, chain-link or twisted strands.

Figure 1:
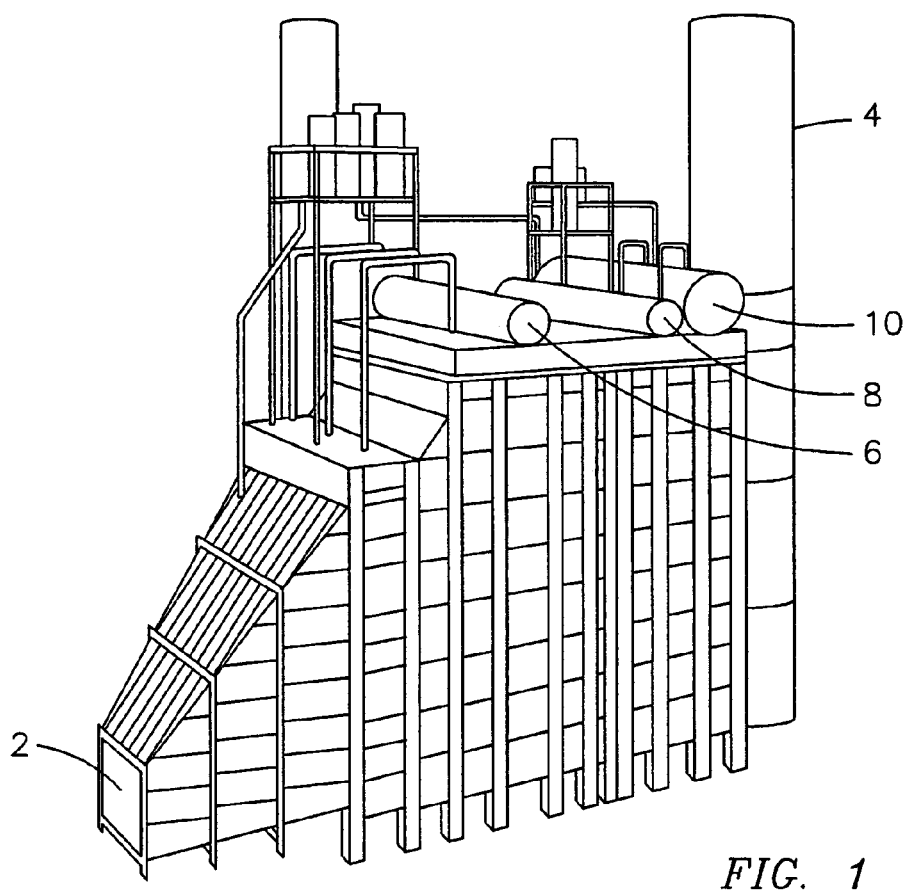
FIG. 1 illustrates a heat recovery steam generator according to the prior art.
Figure 2:
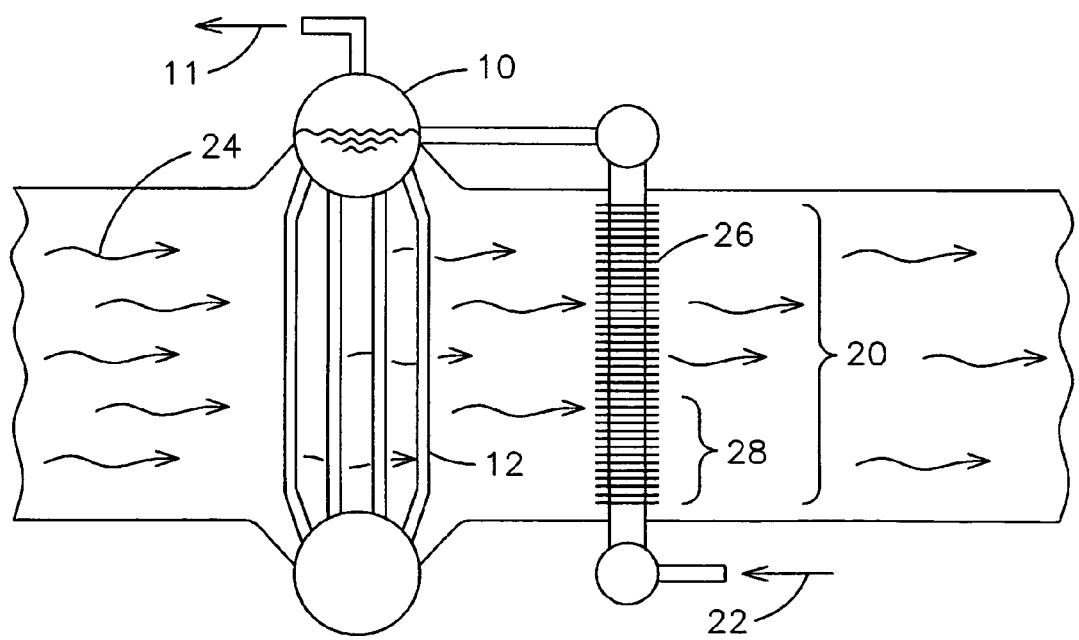
FIG. 2 illustrates a typical boiler tube used in a heat recovery steam generator according to the prior art.

To further increase the accuracy of the measurement of corrosion in relation to coupon thickness, coupons are pulled taut across the monitored part. This limits the exposure to one side of the coupon to the corrosive environment. Also, this allows for thermal conductivity between the coupon and the monitored device. As discussed in FIG. 2, a boiler tube 20 conducts cold water 22 through its center, and is exposed to hot gasses 24 on its exterior. It is the cold nature of the boiler tube that allows for corrosive elements to condense onto its surface. In such circumstances, coupons need to be tight against the boiler tube so that they stay at essentially the same temperature. It is important, however, not to over-stress the coupons, since many materials corrode faster when they are stressed. The material loss monitor may be installed in place for years or decades, so even a small corrosive increase can have a long term effect.

Coupons may be in contact with monitored parts in a variety of different way. They can be wrapped several times around a part to be monitored, or they can touch it on an arc. In FIG. 4 the coupons 34 are attached around the circumference of the boiler tube 20, though in other embodiments they may run partially or completely down the tube's length. In still other embodiments the coupons are placed in the corrosive environment without contact with any specific part. Often parts have contoured surface areas such as fins. The coupons of the present invention can go between the contours and contact the tube where the corrosion is the greatest.

The material of which the coupons are made can be varied depending on the nature of the corrosive environment and the composition of the part to be monitored. Some examples include, but are not limited to, carbon steel, metals and alloys, synthetic fibers and plastics. In particular embodiments, the coupons are made from the same material as the parts that they are monitoring.

As discussed above, some parts in corrosive environments have life expectancies of years or decades. If parts fail early then entire systems can be disrupted. However, if the corrosion levels are estimated too cautiously then efficiency is wasted. By using coupons of varying thickness, the present invention can be used to optimize operation of systems in corrosive environments. For example, in a HRSG, coupons may be arrayed such that they are estimate to break every six month or every year. If coupons are breaking earlier than expected, then the temperature of the gasses surrounding the boiler tube or the temperature of the fluid within the tube can be increased. If the coupons are lasting longer than expected then more of heat from the hot gasses can be recycled.

Figure 5:
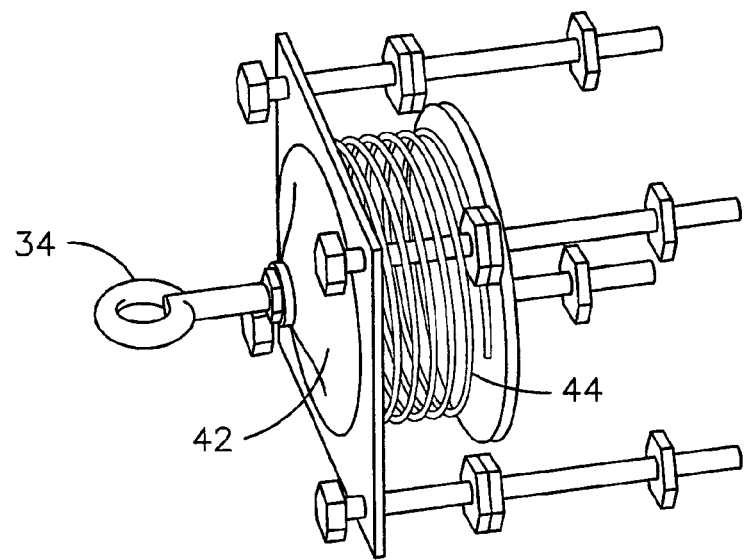
FIG. 5 illustrates one embodiment of a device for determining the failure of a coupon.

Referring to FIG. 5, one embodiment of the monitoring device that detects coupon failure is shown. An eyebolt 34 anchors one end of a coupon (not shown). The tautness of the coupon compresses a tension spring 44. While the coupon remains intact, the tension spring 44 remains compressed. However when the coupon fails, the tension spring 44 releases and closes a circuit (not shown). The tension spring is protected from the corrosive environment by a membrane 42 that prevents corrosive elements from entering the monitoring device. The term tensioned spring as used herein alternately refers to compressed springs.

The monitoring device detects a coupon failure when a circuit is switch from an "off" state to an "on" state. In other embodiments, the failure of a coupon will switch a circuit from an "on" state to an "off" state. In particular embodiments, the coupon itself comprises part of the circuit, so when the coupon is broken the circuit is opened. Extra caution needs to be taken for this embodiment, however, since running an electrical current through a coupon can itself increase corrosion, and the electrical current may fail before the coupon is actually broken.

The monitoring device itself may have its own self monitoring systems. For example, an active circuit within the monitoring device that is susceptible to corrosion will fail if corrosive elements enter the monitoring device. This type of self monitoring circuit can be placed in proximity to vulnerable areas, such as the membrane 42 that protects the tension spring 44 from the corrosive environment. This can be particularly useful in embodiments where a monitoring circuit needs to be turned "on" rather than "off" as described above.

The expression coupon failure as used in the above examples generally refers to the breakage of a coupon from corrosion. However, additional types of failure may also indicate corrosion depending on the embodiment. Such as a slacking of the coupon or a failure to carry a sufficient current.

Figure 6:
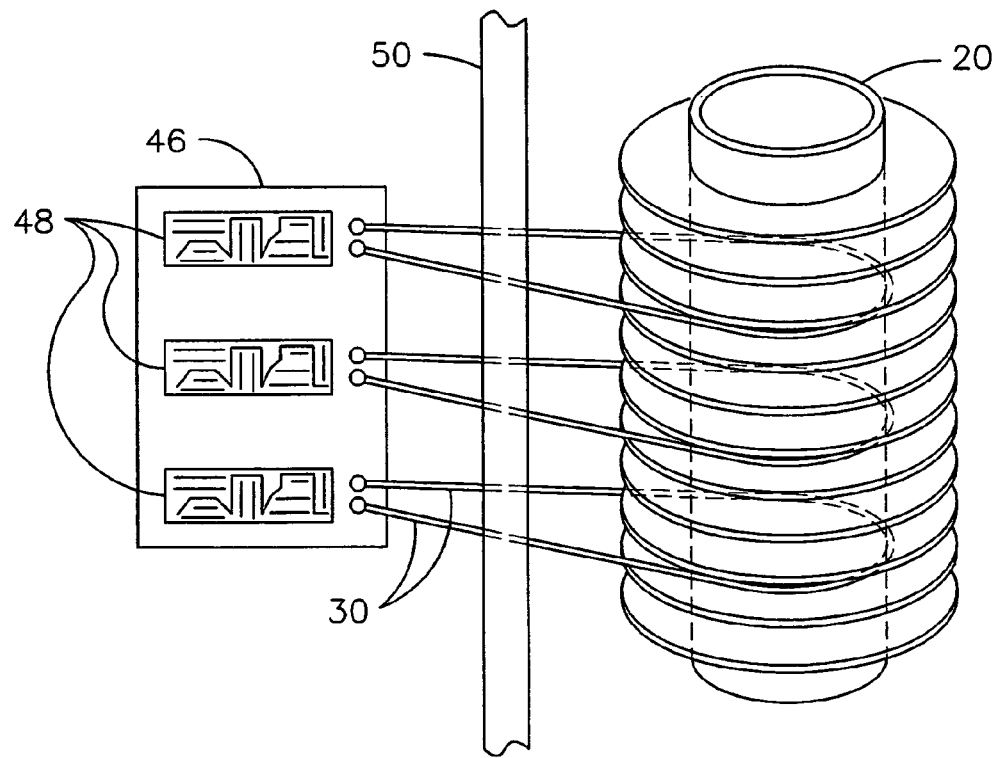
FIG. 6 illustrates an embodiment of a material loss monitor where the device for determining the failure of a coupon is remote from the corrosive environment.

Referring to FIG. 6, one embodiment of a monitoring device 46 that is remotely placed from the corrosive environment is illustrated. Multiple coupons 30 partially wrap the circumference of a boiler tube 20 that is exposed to a corrosive environment. The coupons then leave the corrosive environment through a wall 50 and attach to a remote monitoring device 46. The monitoring device 46 may display the status of the coupons 48 on its face, or transmit the status to a more remote location (not shown). In this embodiment, the ends of the coupons may be physically checked and tightened when necessary.

In one embodiment the present invention provides for a method of monitoring corrosion of a part in a corrosive environment. The method comprises installing on the part multiple coupons of varying thickness, where the coupons are at least in part exposed to the corrosive environment. The coupons are linked to a monitoring device, which may be remote from the corrosive environment, where the monitoring device will register a failure in at least one of the multiple coupons. The failure is then interpreted as an approximate level of corrosion in the part.

In one embodiment the coupons are ribbon-shaped. In a related embodiment, the varying thickness of the coupons is from 0.1" (cm) to the failure thickness of the part. In another embodiment the coupons are in thermal contact with the part, and in a related embodiment the coupons are at least partially wound around the part.

In another embodiment, the monitoring device registers the failure by at least one of the coupons breaking. The breaking of at least one of the coupons releases a tensioned spring, and the release of the tensioned spring closes a circuit. The closing of the circuit then is the registering of the failure. In a particular embodiment each of the multiple coupons has a specific circuit that registers a specific coupon break. In still another related embodiment an electrical current is passed through the coupons, and the monitoring device registers the failure by the coupons breaking, where the breaking of at least one of the coupons interrupts the electrical current. In some instances the corroded coupons may fail to carry the electrical current before breaking, which will also be registered as a failure.

In a particular embodiment the present invention provides for a method and apparatus of monitoring corrosion of a boiler tube in a heat recovery steam generator. The method comprises installing on the boiler tube multiple coupons of varying thickness, where the coupons are at least in part wrapped around a surface of the boiler tube that is exposed to the corrosive environment. The coupons maintain substantial thermal contact with the boiler tube and are linked to a monitoring device. The monitoring device will register a failure in at least one of the coupons, where the failure in at least one of the coupons is a breaking of at least one of the coupons. The registering of the failure of at least one coupon comprises placing a coupon under tension that holds a spring under tension at a terminal end of the coupon, where the breaking of the coupon releases the spring, and the release of the spring closes a particular circuit, and where the closure of the particular circuit indicates a specific failure of a coupon of specific thickness. The specific failure in the coupon of specific thickness is then interpreted as an approximate level of corrosion in the boiler tube. In a more particular embodiment multiple interpretations are made on multiple failures of coupons of specific thickness to determine an approximate level of corrosion in the boiler tube.

In one embodiment the present invention provides an apparatus for monitoring corrosion of a part in a corrosive environment. The apparatus comprises one or more coupons that are exposed to the corrosive environment in a manner similar to the part. The apparatus further comprises a monitoring device that registers a failure in the one or more coupons. The coupons are either mounted to the part, the monitoring device, another feature in the environment or a combination thereof. The failure of a coupon correlates to an approximate level of corrosion in the part.

In a related embodiment, the apparatus comprises multiple coupons, and the monitoring device is capable of registering a separate failure in each of the coupons. The coupons can either be free standing from the part being monitored or they can be in intimate contact with the part.

In another related embodiment, the coupons are of a variety of thickness or a variety of materials, or both. In particular embodiments, the coupons are of the same or similar material as the part being monitored. The coupons can be all attached to the same monitoring device, or multiple monitoring devices can be used. In some embodiment the same coupon is attached to more than one monitoring device.

Though particular embodiments of the invention discussed have focused on HRSG systems and their corresponding boiler tubes, the present invention is equally applicable in other corrosive and erosive environments. The term corrosive, as used herein, includes erosive, caustic, wearing and similar environments. A variety of parts may also be monitored, such as pipes, containers and walls, erosion.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the inventions which, is to be given the full breadth of the claims appended and any and all equivalents thereof.

What is claimed is:

1. A method for monitoring corrosion of a part in a corrosive environment comprising:
    installing on said part a plurality of coupons of varying thickness, wherein said coupons are at least in part exposed to said corrosive environment, wherein said coupons are at least partially in thermal contact with said part, and wherein said coupons are at least partially wound around said part;
    linking said coupons to a monitoring device, wherein said monitoring device will register a failure in at least one of said plurality of coupons; and
    interpreting said failure in at least one of said plurality of coupons as an approximate level of corrosion in said part.

2. The method of claim 1, wherein said plurality of coupons are ribbon-shaped.

3. The method of claim 1, wherein said failure of at least one of said plurality of coupons consists of a breaking of at least one of said plurality of coupons.

4. The method of claim 1, wherein the varying thickness of said coupons is from 0.1" (0.25 cm) to the failure thickness of said part.

5. The method of claim 4, wherein each of said plurality of coupons has a specific circuit that registers a specific coupon break.

6. The method of claim 5, wherein an electrical current is passed through said plurality of coupons, and wherein said monitoring device registers said failure by at least one of said coupons breaking, wherein the breaking of at least one of said coupons interrupts said electrical current.

7. A method for monitoring corrosion of a part in a corrosive environment comprising:
    installing on said part a plurality of coupons of varying thickness, wherein said coupons are at least in part exposed to said corrosive environment;
    linking said coupons to a monitoring device, wherein said monitoring device will register a failure in at least one of said plurality of coupons; and
    interpreting said failure in at least one of said plurality of coupons as an approximate level of corrosion in said part;
    wherein said monitoring device registers said failure by at least one of said coupons breaking, wherein the breaking of at least one of said coupons releases a tensioned spring, and wherein the release of said tensioned spring closes a circuit, wherein the closing of said circuit is the registering of said failure.

8. The method of claim 1, wherein said coupons are made of a similar material to said part.

9. The method of claim 1, wherein said monitoring device is remote from said corrosive environment.

10. A method for monitoring corrosion of a boiler tube in a heat recovery steam generator comprising:
    installing on said boiler tube a plurality of coupons of varying thickness, wherein said coupons are at least in part wrapped around a surface of said boiler tube that is exposed to a corrosive environment within said heat recovery steam generator, wherein said coupons maintain substantial thermal contact with said boiler tube;
    linking said coupons to a monitoring device, wherein said monitoring device will register a failure in at least one of said plurality of coupons, wherein said failure in at least one of said plurality of coupons is a breaking of at least one of said plurality of coupons;

wherein the registering of said failure of at least one coupon comprises placing a coupon under tension that holds a spring under tension at a terminal end of said coupon, wherein said breaking of said coupon releases said spring, and the release of said spring closes a particular circuit, wherein the closure of said particular circuit indicates a specific failure of a coupon of specific thickness; and interpreting said specific failure in said coupon of specific thickness as an approximate level of corrosion in said boiler tube.

11. The method of claim 10, wherein a plurality of interpretations are made on a plurality of failures of coupons of specific thickness to determine an approximate level of corrosion in said boiler tube.

12. An apparatus for monitoring corrosion of a part in a corrosive environment comprising:
at least one coupon;
a mount for said coupon; and
a monitoring device operatively coupled to said coupon such that it is capable of registering a failure in said coupon;
wherein said coupon is exposed to said corrosive environment in a manner similar to said part, wherein said coupons are at least partially in thermal contact with said part, and wherein said coupons are at least partially wound around said part;
wherein said failure of said coupon correlates to an approximate level of corrosion in said part.

13. The apparatus of claim 12, wherein said apparatus comprises a plurality of coupons, wherein said monitoring device is capable of registering a separate failure in each of said plurality of coupons and wherein said separate failure of said plurality of coupons correlates to an approximate level of corrosion in said part.

14. The apparatus of claim 13, wherein said plurality of coupons are of a variety of materials.

15. The apparatus of claim 13, wherein said apparatus further comprises a plurality of monitoring devices.

16. The apparatus of claim 12, wherein said coupon is made of a similar material to said part.

17. The apparatus of claim 12, wherein said coupon is in intimate contact with said part.

* * * * *